(12) United States Patent
Green et al.

(10) Patent No.: US 7,892,732 B2
(45) Date of Patent: Feb. 22, 2011

(54) METHOD OF PERFORMING PCR AMPLIFICATION ON A MICROARRAY

(75) Inventors: Roland Green, Madison, WI (US); Thomas J. Albert, Madison, WI (US)

(73) Assignee: Roche Nimblegen, Inc., Wilmington, DE (US)

( * ) Notice: Subject to any disclaimer, the term of this patent is extended or adjusted under 35 U.S.C. 154(b) by 111 days.

(21) Appl. No.: 11/034,374

(22) Filed: Jan. 12, 2005

(65) Prior Publication Data
US 2005/0227263 A1 Oct. 13, 2005

Related U.S. Application Data

(60) Provisional application No. 60/535,982, filed on Jan. 12, 2004.

(51) Int. Cl.
*C12Q 1/68* (2006.01)
*C12P 19/34* (2006.01)
(52) U.S. Cl. .......................... 435/6; 435/91.2
(58) Field of Classification Search ............ None
See application file for complete search history.

(56) References Cited

U.S. PATENT DOCUMENTS 6,300,070 B1 * 10/2001 Boles et al. ............... 435/6
6,375,903 B1 * 4/2002 Cerrina et al. ............. 422/131
6,618,679 B2 * 9/2003 Loehrlein et al. .......... 702/20
2003/0068633 A1 * 4/2003 Belshaw et al. ............ 435/6

FOREIGN PATENT DOCUMENTS

WO WO 96/04404 2/1996
WO WO 03/060159 7/2003

OTHER PUBLICATIONS

Strizhkov et al. PCR amplification on a microarray of gel-immobilized oligonucleotides: detection of bacterial toxin- and drug-resistant genes and their mutations. BioTechniques (2000) 29:844-857.*
Albert, T.J., et al.,"Light-directed 5'-3' synthesis of complex oligonucleotide microarrays," Nucleic Acids Research 31:E35.1-E35.9 (2003).
Beier, M., et al., "Analysis of DNA-microarrays produced by inverse in situ oligonucleotide synthesis," Journal of Biotechnology 94:15-22 (2002).
Pemov, A., et al., "DNA analysis with jultiplex microarray-enhanced PCR," Nucleic Acids Research 33:E11.1-E11.9 (2005).

* cited by examiner

*Primary Examiner*—Kenneth R. Horlick
*Assistant Examiner*—David C Thomas
(74) *Attorney, Agent, or Firm*—Quarles & Brady LLP

(57) ABSTRACT

The present invention provides a method of amplifying target DNA by PCR or multiplex PCR on a microarray using array-immobilized DNA probes synthesized in a common area on the microarray by a maskless array synthesizer (MAS). The MAS constructed array-immobilized DNA probes include a universal primer linked to a sequence-specific probe, and optionally a calibrated probe for use in quantifying amplified target DNA.

2 Claims, 3 Drawing Sheets

METHOD OF PERFORMING PCR AMPLIFICATION ON A MICROARRAY

CROSS-REFERENCE TO RELATED APPLICATIONS

This application claims the benefit of U.S. Provisional Application No. 60/535,982 filed Jan. 12, 2004. The provisional application is incorporated herein by reference in its entirety.

STATEMENT REGARDING FEDERALLY SPONSORED RESEARCH OR DEVELOPMENT

Not Applicable

BACKGROUND OF THE INVENTION

DNA microarray technology has been applied to many areas such as gene expression and discovery, mutation detection, allelic and evolutionary sequence comparison, genome mapping and more. Unfortunately, most applications fail to tap into the full capacity of microarray technology as many hybridization assays involve far less probes than are available using the full capability of the number of features possible in a high density microarray.

The advent of DNA microarray technology makes it possible to build an array of hundreds of thousands of DNA sequences in a very small area, such as the size of a microscopic slide. See, e.g., U.S. Pat. No. 6,375,903 and U.S. Pat. No. 5,143,854, each of which is hereby incorporated by reference in its entirety. The disclosure of U.S. Pat. No. 6,375,903 enables the construction of so-called maskless array synthesizer (MAS) instruments in which light is used to direct synthesis of the DNA sequences, the light direction being performed using a digital micromirror device (DMD). Using an MAS instrument, the selection of DNA sequences to be constructed in the microarray is under software control so that individually customized arrays can be built to order. In general, MAS-based DNA microarray synthesis technology allows for the parallel synthesis of over 800,000 unique oligonucleotide features in a very small area on a standard microscope slide.

Many applications require looking at markers across the entire human genome. The genome is typically too complex to be studied as a whole, and thus techniques must be used to reduce the complexity of the genome. A common technique that is often used is to amplify regions of the genome by Polymerase Chain Reaction (PCR).

This, however, requires that each section of the genome be amplified in either individual or multiple PCR reactions also known as multiplex PCR in a reaction tube. Conducting multiplex PCR in a tube, however, is limited to at most a few hundred reactions. Each primer pair for each reaction must be synthesized serially, quality controlled, and cataloged. Each unique primer must then be added to each reaction in the appropriate combination. This adds significant expense and time for each multiplex PCR reaction. Thus, it would be advantageous to be able to synthesize a plurality (i.e., thousands to tens of thousands) of DNA probes on an array to amplify a plurality of DNA target sequences present in a sample.

The DNA microarrays are generally synthesized by using light to direct which oligonucleotides are synthesized at specific locations or features on an array. Typically, only one nucleotide sequence is synthesized at each feature of the array, even though there are multiple DNA probes in each feature. This is because all the DNA probes in each feature have the same nucleotide sequence. However, in order to perform PCR on the array, two different oligonucleotide sequences must be synthesized in the same array feature. Accordingly, methods for amplifying DNA on a microarray are disclosed.

BRIEF SUMMARY OF THE INVENTION

The present invention is summarized as a method of amplifying target DNA on a microarray using PCR. The method uses array-immobilized DNA probes, constructed using a maskless array synthesizer in a common area of the microarray, wherein the array DNA probes have a universal primer, a sequence-specific probe, and optionally a calibrated probe sequence, for quantifying amplified target DNA. A sample containing target DNA sequence(s) along with a sufficient amount of amplification reagents are added to the array-immobilized probes to initiate amplification. Through multiple rounds of thermal cycling non-array target DNA are produced having universal primer(s) and sequence-specific probe(s) the flanking target DNA sequence(s) of interest.

Thus, in one aspect, the invention provides a method of performing multiplex PCR on a microarray. The method is practiced by providing a plurality of array probes immobilized on a common area of the microarray. The universal primers on each of the plurality of array probes are identical across each common area on the microarray and each sequence-specific probe of each immobilized array probe is unique to a genomic region and different across each common area on the microarray. Accordingly, when a sample of target DNA sequences is added to a common area under reaction conditions suitable for multiplex PCR amplification, a plurality of unique target DNA sequences may be simultaneously amplified.

In another aspect, the invention provides a method of quantifying target DNA sequences amplified by PCR or multiplex PCR on a microarray by synthesizing a calibration probe sequence between the universal primer and the sequence-specific probe of an immobilized array probe. Then, upon amplification the resultant amplification product would include a calibrated probe that can be used to quantify target sequence in a sample.

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used.

Other objects, advantages and features of the present invention will become apparent from the following specification taken in conjunction with the accompanying drawings.

DETAILED DESCRIPTION OF THE INVENTION

The present invention broadly relates to a method of amplifying target DNA sequence on a microarray using PCR or multiplex-PCR. The method employs at least two array-immobilized probes each of which is a combination of a universal primer, a sequence-specific probe, and optionally a calibrated probe sequence to quantify amplified target DNA. Each array-immobilized probe is synthesized in a feature or common area on the microarray using a maskless array synthesizer. A sample containing target DNA along with a sufficient amount of amplification reagents are added to each common area on the microarray containing the array-immobilized probes. Then, target DNA amplification is initiated by hybridizing complementary region(s) of sample target DNA sequence(s) to sequence-specific probe(s). Then multiple rounds of thermal cycling produce non-array target DNA strand(s) having universal primer(s) and sequence-specific probe(s) flanking amplified target DNA sequence(s) of interest.

Figure 2A:
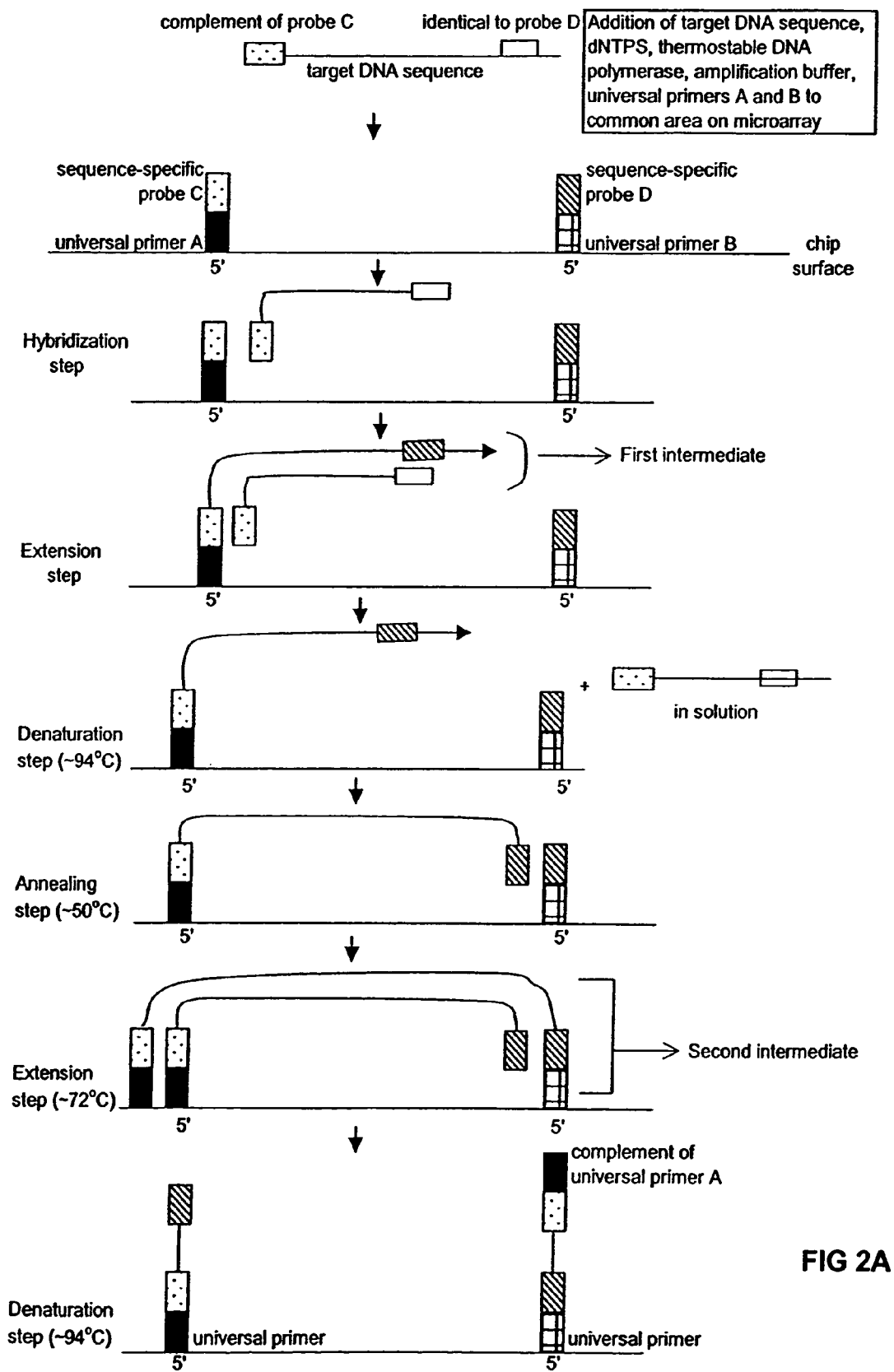
FIG. 2A-B is a schematic view of a method of performing PCR on a microarray.

Accordingly, in the simplest embodiment the invention provides a method of amplifying a target DNA sequence on a microarray using PCR. This embodiment is exemplified in FIG. 2A-B. As shown in FIG. 2A, the method provides two array-immobilized probe each having a combination of a universal primer linked to a sequence-specific probe synthesized in a common area of the microarray using a maskless array synthesizer.

The term "target DNA sequence" as used herein refers to a region of a genome that is to be studied. Target DNA sequence (s) of interest are contained in a sample which include nucleic acids from any source in purified or unpurified form. Although, the target DNA may be from any source, genomic DNA is most suitable.

Also, the target DNA sequence can be any nucleic acid sequence of any size, preferably derived from natural sources, but can be synthesized chemically. The target DNA may include, but is not limited to, double-stranded DNA (dsDNA) and single-stranded DNA (ssDNA), such as chromosomes, the genomes of plants, mammals, bacteria, yeasts, viruses, viroids, mycoplasma, molds, or other microorganisms. DNA from mammals may include human and forensic samples, such as blood, semen, vaginal swabs, tissue, hair, saliva, urine and mixtures of body fluids. Target DNA can also be obtained from a complex mixture of DNA and RNA, including, but not limited to, mixtures of the above nucleic acids or fragments thereof or DNA-RNA hybrids. Accordingly, methods for purification of target DNA, if further purification is necessary, are also known in the art.

Furthermore, if the target DNA sequence is a dsDNA, prior to adding sample target DNA to the common area of the microarray, the target DNA is preferably denatured rendering the target DNA single-stranded. The denaturation step may be thermal denaturation or any other method known in the art, such as alkali treatment. Thus, in some embodiments of the invention, the ssDNA target sequence may include either ssDNA that is present in a biological sample or ssDNA that is obtained by denaturation of dsDNA in the sample.

Also, in accordance with the invention, the term "sequence-specific probe" as used herein refers to a ssDNA sequence linked to an array-immobilized universal primer. There are generally two sequence specific probes per target DNA sequence in a sample to be amplified. Each pair of sequence-specific probe is referred to herein as a first or second sequence-specific probe. Typically, a first sequence-specific probe will be complementary to the 5'-end of a target DNA sequence to be amplified in a sample and the second sequence-specific probe will be identical to the 3'-end of the target DNA sequence in the sample to be amplified. Suitable sequence-specific probes may be identified, using bioinformatics techniques known to those skilled in the art.

It is noted that the exact length of each sequence-specific probe will depend on many factors relating to the ultimate function and use of the probe, including temperature, source of the probe and use of the method. The probe can occur naturally through a purified restriction digest, or be produced synthetically. The probe is capable of acting as an initiation point for synthesis when placed under conditions inducing synthesis of a primer extension product complementary to a nucleic acid strand. The primer extension conditions can include the presence of nucleotides and a DNA polymerase at a suitable temperature and pH. In a preferred embodiment, the probe is a single-stranded oligodeoxyribonucleotide of sufficient length to initiate the synthesis of an extension product from a specific sequence in the presence of a DNA polymerase. Sensitivity and specificity of the probes may be determined by the primer length and uniqueness of the sequence within a given sample. In the present invention the sequence-specific probes are about greater than 15 oligonucleotides and in the preferred embodiment are about 20 to 30 oligonucleotides in length.

Alternatively the term "universal primer" as used herein refers to a DNA sequence immobilized to the common area of the microarray. It is noted that in practicing the invention, each immobilized universal primer is linked to a unique sequence-specific probe. A universal primer is meant to encompass any nucleic acid that is capable of initiating the synthesis of a nascent nucleic acid in a template-dependent process.

Universal primers are oligonucleotides from ten to twenty or thirty base pairs in length, such as T7, T3, M13, and SP6 among others. It is also envisioned that at least one nucleotide of the universal primer, which is complementary to one of the amplification products may have a detectable label, suitably a fluorescent label.

Figure 1:
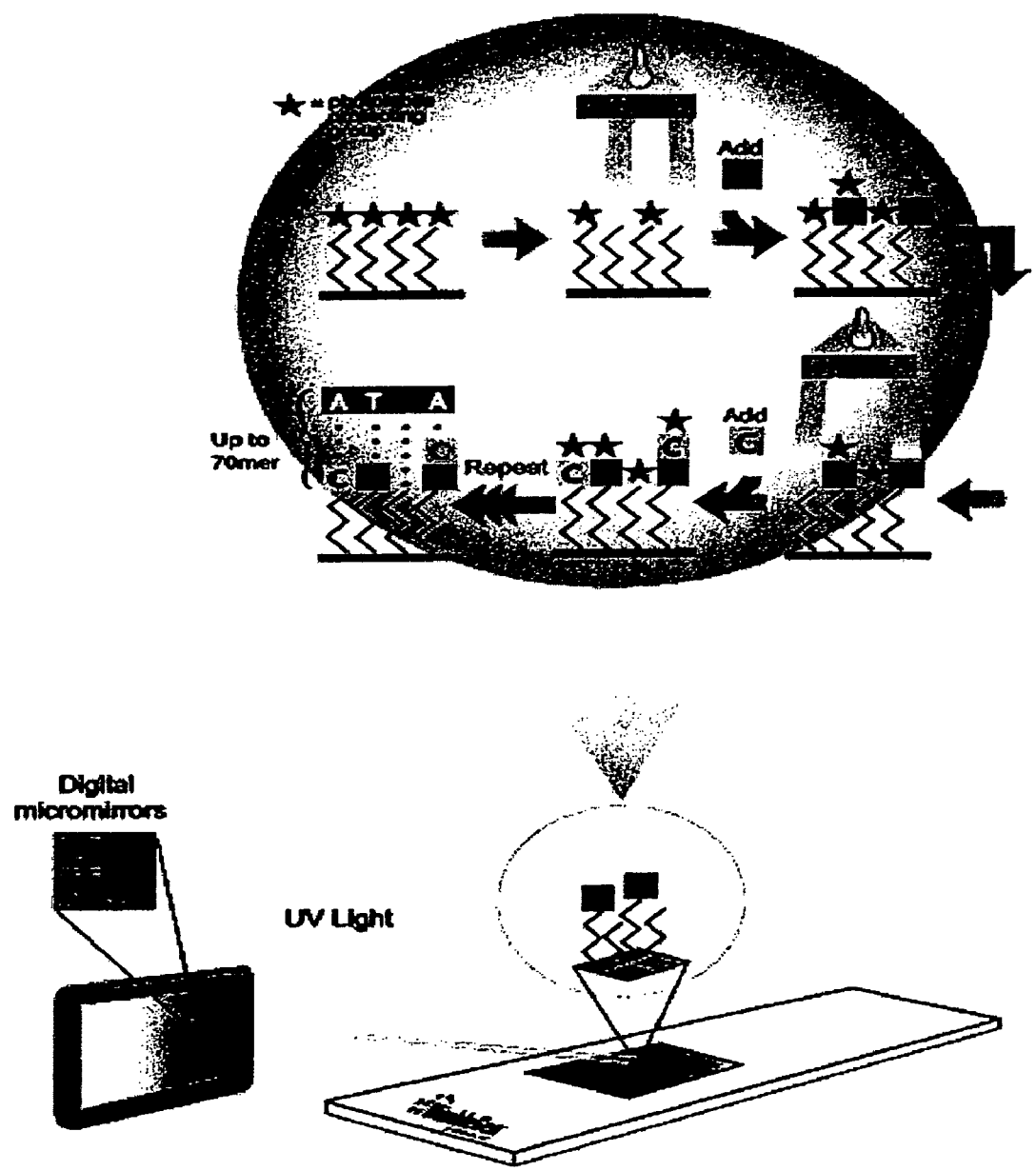
FIG. 1 is a depiction of DNA microarray synthesis.

Furthermore, the term "maskless array synthesizer" or "MAS" as used herein refers to an apparatus employed to produce DNA probe microarrays, first synthesized according to the methods described in U.S. Pat. No. 6,375,903 (incorporated by reference herein in its entirety). The array probes (e.g., a combination of a universal primer, a sequence-specific probe, and optionally a calibrated probe sequence) are synthesized one nucleotide at a time in the common area of the microarray using MAS instrument. In brief, the MAS instrument is a digital method of high-density DNA microarray manufacture based on "virtual masks" that exist only as graphics files that describe the pattern of light required for a given photodeprotection step. The digital graphics files are sent in synchrony with the synthesis chemistry to a digitally addressable micromirror array containing 786,432 (1024× 768) individual polished aluminum 17×17 mm mirrors to generate the required light patterns in the synthesized sequence. The DNA microarray synthesis technology is depicted in FIG. 1. In referring to FIG. 1, the TV light source is reflected by the mirror array in locations where photo-deprotection is required. Also, the inset shows a graphical depiction of the sequential spatially addressed addition of nucleotides to the growing array. Thus, the maskless array synthesizer facilitates amplification of target DNA on a microarray through the synthesis of a plurality of array-immobilized DNA probe combinations.

Once the array-immobilized DNA probes are synthesized on common areas or features of the microarray, then one or more of the following compositions may be added to the common area such as a sample non-array target DNA sequence as described above and a sufficient amount of amplification reagents. It may be desirable to remove RNA from the sample before applying it to the array. Such can be accomplished by digestion with DNase-free RNase.

The amplification reagents include deoxynucleotides (dNTPS), thermostable DNA polymerase, amplification buffer, and a pair of non-array universal primers, which are complementary to one of the amplification products, and the necessary co-factors for the amplification reaction(s). Accordingly, the amplification is carried out in a common area of a microarray in a chamber allowing temperature cycling. It is envisioned that amplification may be carried out such that each individual common area is performed in a custom reaction chamber, and may or may not be covered in oil.

After the amplification reagents have been added to the array probes in the common area, amplification of target DNA proceeds under suitable reaction conditions. Such conditions are known or readily established by those of skill in the art, and can be exemplified by the reaction conditions used in U.S. Pat. Nos. 4,683,202, 4,683,195, and 4,800,159, which are incorporated herein by reference. As one example and not to limit the invention, suitable reaction conditions can comprise: 0.2 mM each dNTP, 2.2 mM $MgCl_2$, 50 mM KCl, 10 mM Tris-HCl pH 9.0, 0.1% Triton X-100.

In particular, the temperature is suitably adjusted to allow the complementary region of the non-array target DNA sequence to anneal to the first sequence-specific probe under conditions suitable for hybridization. It is noted that a region of the target DNA sequence is complementary to the first sequence-specific probe and an opposite region of the target DNA sequence is identical to the second sequence-specific probe. Thus, in accordance, with the invention, the terms "hybridize" or "anneal" refer to the formation of complexes between nucleotide sequences on opposite or complementary nucleic acid strands that are sufficiently complementary to form complexes via Watson-Crick base pairing. The annealing step is suitably conducted between a range of about 40° C. to 55° C.

Figure 2B:
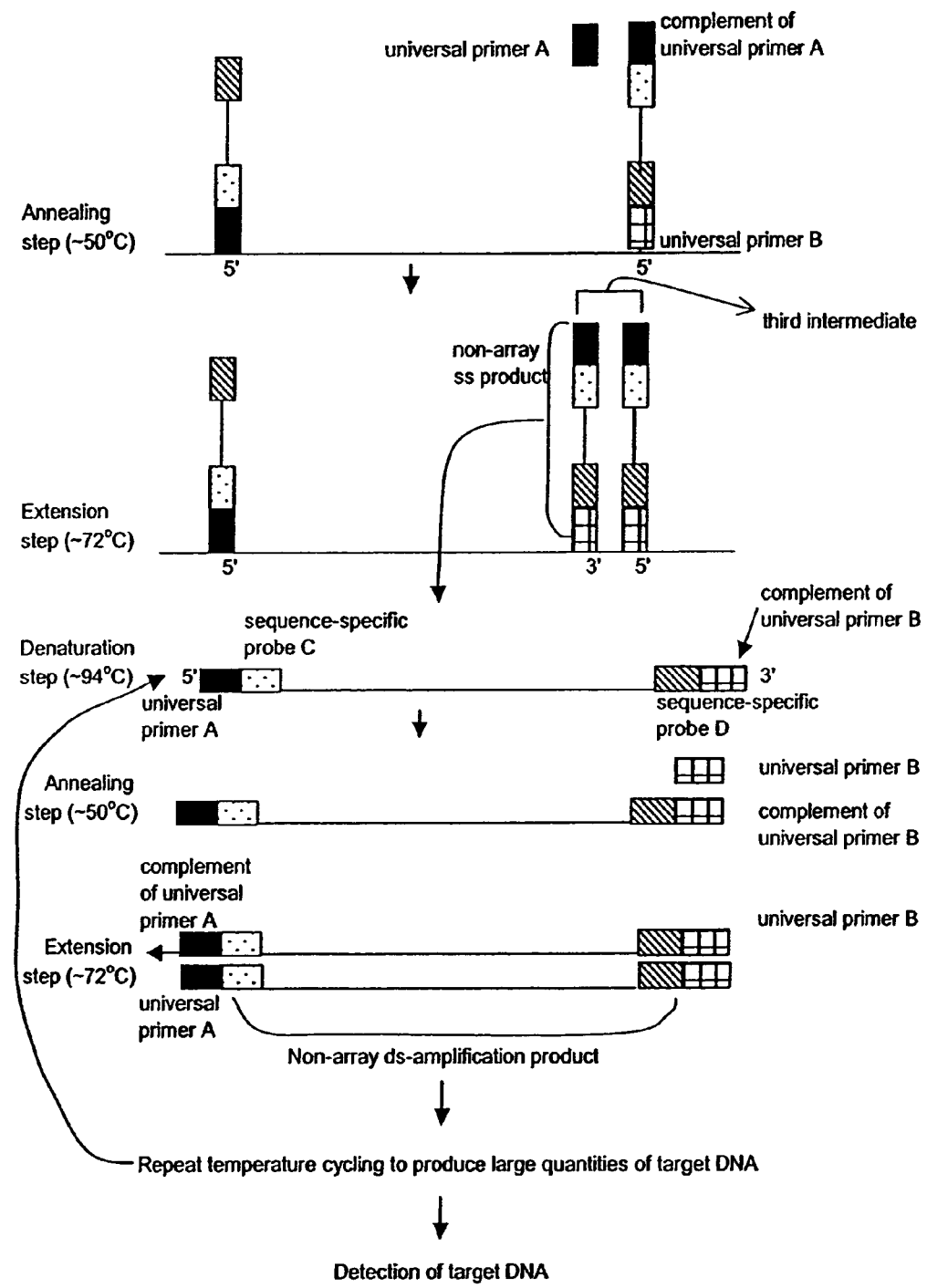

Once, the first sequence-specific probe is annealed to the complementary region of the target DNA sequence strand extension is initiated by a suitable thermal stable DNA polymerase. Suitably, the extension step is conducted between a range of about 65° C. to 75° C. The synthesized or extended copy is complementary to the target DNA sequence, thus, forming a duplex, suitably a "first intermediate," having a first array strand, encompassing a region that is complementary to the second sequence-specific probe, as shown in FIG. 2A-B. In referring to FIG. 2A-B, it is further noted that DNA is always synthesized in the 5'-to-3' direction and the two strands of a DNA duplex always are aligned so that the 5'-ends of the two strands are at opposite ends of the duplex and, by necessity, so then are the 3'-ends.

Next, the first intermediate is heat denatured, suitably between about 85° C. to 100° C., such that the sample non-array target DNA sequence is released into the common area. The complementary region of the first array strand is annealed to the second sequence-specific probe. The second sequence-specific probe is extended to form a "second intermediate" having a second array strand, such that the second array strand encompasses a region that is complementary to the first array probe, including the first universal primer. The second intermediate is denatured to form two single-stranded array-immobilized strands, the first array strand and the second array strand. Then, as shown in FIG. 2B, the non-array first universal primer mobile in the common area is annealed to the complement of the first universal primer on the second array strand. The non-array first universal primer is extended to form a "third intermediate," having an array strand and a complementary mobile or non-array strand, such that the non-array strand encompasses the first and second array probes spanning the target DNA sequence of interest. The third intermediate, as shown in FIG. 2B is then denatured such that the mobile, non-array strand in the liquid phase of the common area becomes available to serve as a template for conducting multiple rounds of thermal cycling, suitably by PCR in the liquid phase, above the surface of the common area on the microarray.

As used herein the term "PCR" refers to a method whereby virtually any target DNA sequence can be selectively amplified. The method uses forward and reverse sequence-specific probe pairs specific for regions which flank a target DNA sequence which hybridize to opposite strands of target DNA and define the limits of the sequence to be amplified. The specifically designed oligonucleotides initiate multiple sequential rounds of DNA synthesis catalyzed by a thermostable DNA polymerase, such as *Thermus apuaticus* (Taq) polymerase or *Thermococcus litoralis* (Vent™, New England Biolabs) polymerase or TthI polymerase (Perkin-Elmer). Each round of synthesis is typically separated by a melting and re-annealing step, allowing a given DNA sequence to be amplified several hundred-fold in less than an hour.

Methods for PCR amplification are described in the art (PCR Technology: Principles and Applications for DNA Amplification ed. H A Erlich, Stockton Press, New York, N.Y. (1989); PCR Protocols: A Guide to Methods and Applications, eds. Innis, Gelfland, Snisky, and White, Academic Press, San Diego, Calif. (1990); Mattila et al. (1991) Nucleic Acids Res. 19: 4967; Eckert, K. A. and Kunkel, T. A. (1991) PCR Methods and Applications 1: 17; and U.S. Pat. Nos. 4,683,202 and 4,965,188, each of which are incorporated herein by reference).

The simplicity and reproducibility of PCR amplification reactions has given PCR broad applicability. For example, PCR has gained widespread use for the diagnosis of inherited disorders, susceptibility to disease and forensic analysis, among others. Typically, the genomic region of interest is amplified, mutations or polymorphisms are then identified by subjecting the amplified DNA to analytical techniques such as DNA sequencing, hybridization with allele specific oligonucleotides, restriction endonuclease cleavage or single-strand conformational polymorphism (SSCP) analysis.

For the analysis of small genes or genes where the mutant allele or polymorphism is well characterized, amplification of single defined regions of DNA is sometimes sufficient. However, when analyzing large and/or undefined genes, multiple individual PCR reactions are often required to identify critical base changes or deletions. Thus, to streamline the analysis of large complex genes, "multiplex PCR" (i.e., the simultaneous amplification of different target DNA sequences in a single PCR reaction) has been utilized.

Also, it is envisioned that the target DNA sequence products generated by the methods of the invention may be modified or differentially labeled suitable for detection by visual means using standard methods known to those of skill in the art. Typically, amplification product is labelled either in the course of amplification or subsequently. The term "differentially labeled" indicates that each extension product leading to the final amplified DNA products can be distinguished from all others because it would have a different label attached and/or is of a different size and/or binds to a specifically labeled oligonucleotide.

One skilled in the art will recognize that a variety of labels are available. For example, these can include radioisotopes, fluorescers, chemiluminescers, stains, enzymes and antibodies. Various factors may affect the choice of the label. These include the effect of the label on the rate of hybridization and binding of the sequence-specific probe to the target DNA sequence, and the sensitivity of the label, among others. For example, differential radioisotope labeling could include $^{32}$P, $^3$H and $^{14}$C; differential fluorescers labeling could include fluorescein-5-isothiocyanate, tetramethylrhodamine-5- (and -6) isothiocyanate, Texas Red and NBD aminoheanoic acid; or a mixture of different labels such as radioisotopes, fluorescers and chemiluminescers.

Finally, the amplified reaction products may be analyzed using any of several methods that are well-known in the art. Preferably, agarose gel electrophoresis may be used to rapidly resolve and identify each of the amplified sequences. For example, in a multiplex PCR reaction, different amplified sequences of different sizes can be resolved in a single gel. Also, prior to sequence analysis, the reaction mixture product may be treated with one or more restriction endonucleases. Alternative methods of product analysis may include without limitation dot-blot hybridization with allele-specific oligonucleotides.

As further described below, this basic concept of amplifying target DNA sequences in a common area on a microarray can be applied to multiplex PCR such that thousands to tens of thousands of DNA targets in a sample may be simultaneously amplified in the common area. Thus, in another embodiment, the invention provides a method of simultaneous amplification of multiple DNA target sequences in a common area of a microarray through multiplex PCR. Contrary to performing traditional PCR on a microarray, in practicing multiplex PCR, a plurality of array-immobilized probes having the same universal primers linked to unique sequence-specific probe are contacted by a DNA sample(s) having multiple target DNA sequences of interest in the same amplification reaction in the common area. As used herein, the term "plurality" refers to at least two or more pairs of array-immobilized probes each having a sequence-specific probe that is unique to a region of a genome to be amplified.

Use of such unique probes makes it possible to simultaneously amplify many different genomic sequences, both short (see U.S. Pat. No. 5,843,660) and long. Such simultaneous amplification is performed under suitable multiplex PCR conditions, known to those of ordinary skill in the art (see U.S. Pat. Nos. 5,364,759 and 5,882,856, both of which are fully incorporated by reference.)

In practicing multiplex PCR, a sequence-specific probe should be designed so that its predicted hybridization kinetics are similar to those of the other probes used in the same common area or feature of the microarray. It is recognized in the art that while the annealing temperatures and primer concentrations may be calculated to some degree, conditions generally have to be empirically determined for each multiplex reaction performed in a common area.

It is noted that in the multiplex reaction buffer, a Taq Polymerase additive known the art, may be added to decrease the competition among amplification products and increase the amplification of longer target DNA during multiplex PCR. Also, although, multiplex PCR requires extensive optimization of annealing conditions for maximal amplification efficiency of the different sequence-specific probes—target DNA sequence template systems, there are PCR reagents, such as buffers having a balanced combination of NH4+ and K+. Such buffers, widen the temperature window for optimal annealing and have been shown to efficiently amplify different sequence-specific probe/target DNA sequence systems with little or no need for optimization of annealing conditions.

Once all of the amplification reagents are added to each common area, then co-amplification of multiple target DNA sequences occurs in one or more cycles of identical denaturing, annealing and extending temperatures and times. Then a plurality of amplified target DNA sequences are obtained. for use in further processing or applications. It is noted that the universal primers are synthesized the same across each common area or feature of the microarray. However, each sequence-specific probe is unique to a specific region of a genome and to sections of the microarray (i.e., one or more array common areas or features).

Also, similar to PCR, if the multiplex PCR product yields are lower than expected, it is envisioned that several options are available to improve yield. They are to perhaps decrease annealing temperature in small steps (2° C.); increase annealing time; increase template concentration; increase overall primer concentration; adjust the DNA polymerase concentration; and to increase the number of PCR cycles or any combination thereof.

Multiplex PCR on a microarray has numerous applications. These include large-scale genotyping analysis, such as mutation analysis of genes in DNA profiling for research, diagnostic, and forensic applications. These kinds of studies are performed by clinical, academic, government, and industrial researchers. Thus, the method of the invention would provide a profound decrease in the amount of time required to provide results and the amount of labor required to produce the results.

In yet another embodiment, the invention provides a method for quantifying PCR or multiplex PCR amplified target DNA sequences on a microarray. Generally, calibration of a PCR reaction is done by co-amplification of a known quantity of a control sequence using the same primers to provide an internal standard that may be used to calibrate the PCR reaction. This is to ensure that the amplification products are produced in approximately the same molar ratio as the starting ratio of templates. The probe array then includes probes specific to the internal standard for quantification of the amplified nucleic acid (see for example, U.S. Pat. No. 6,368,799).

Alternatively, the method is generally practiced, as described above, by constructing immobilized array probes in a common area of a microarray by a maskless array synthesizer. However, in this embodiment a calibration probe sequence would also be synthesized between the universal primer and the sequence-specific probe of the immobilized array probes. The term "calibration probe sequence" as used herein refers to a known sequence and amount of nucleic acid sequence having a length between 10 to 30 nucleotides. They are useful to provide a quantitation reference and permit determination of a standard curve for quantifying the amplified PCR or multiplex PCR target sequence amounts (concentrations).

In particular, as described above a sample having non-array target DNA sequences and a sufficient amount of amplification reagents would be added to a common area on the microarray. Next, through multiple rounds of thermal cycling non-array target DNA sequences are produced (the resultant PCR or multiplex PCR amplification products) having a universal primer, a calibrated probe sequence and a sequence-specific probe flanking each end of the amplified target DNA sequence to be analyzed. Thus, the incorporation of the calibrated probe into the immobilized array probes enables the resultant amplification products to include a calibrated probe that can be used to quantify target DNA sequence in a sample.

The quantification of the resultant calibrated PCR products may be performed using a variety of techniques known in the art, such as gel electrophoresis. The amplified calibrated product may be used in applications to absolutely quantify the copy number for a target sequence in a sample. This would enable quantitative quality control of the target DNA synthesized by PCR amplification.

Furthermore, it is feasible that transcriptions levels can be quantified absolutely using calibration probes. If the calibrated PCR product is used as a template for in vitro transcription, the calibrated probe may be incorporated into the transcript. This calibrated probe could act as a reporter for the concentration of the transcript. Thus, absolute quantification can be accomplished by inclusion of known concentration(s) of target sequences and referencing the amplification intensity of unknowns with the known target sequences (e.g. through generation of a standard curve).

All publications and patents mentioned in the above specification are herein incorporated by reference. Various modifications and variations of the described method and system of the invention will be apparent to those skilled in the art without departing from the scope and spirit of the invention. It is understood, however, that examples and embodiments of the present invention set forth above are illustrative and not intended to confine the invention. The invention embraces all modified forms of the examples and embodiments as come within the scope of the following claims.

We claim:

1. A method of amplifying a target DNA sequence on a microarray, the method comprising:
   (a) synthesizing first and second 5' end immobilized array probes in a common area on the microarray using a maskless array synthesizer, the first array probe having a first universal primer linked to a first sequence-specific probe complementary to a region flanking the target DNA sequence, the second array probe having a second universal primer linked to a second sequence-specific probe identical to a region flanking the opposite end of the target DNA sequence;
   (b) adding to the common area a sample non-array target DNA sequence and a sufficient amount of amplification reagents comprising a non-array first universal primer and a non-array second universal primer;
   (c) annealing the complementary region of the non-array target DNA sequence to the first sequence-specific probe;
   (d) extending the first sequence-specific probe to form a first array strand of a first intermediate, whereby the first array strand comprises a region complementary to the second sequence-specific probe;
   (e) denaturing the first intermediate to release the sample non-array target DNA sequence into the common area;
   (f) annealing the complementary region of the first array strand to the second sequence-specific probe such that the first array strand immobilized to the microarray is annealed to the second sequence-specific robe;
   (g) extending the second sequence-specific probe to form a second array strand of a second intermediate, whereby the second array strand comprises a region complementary to the entire first array probe, including the first universal primer;
   (h) denaturing the second intermediate to form two single-stranded array-immobilized strands such that one of the two single-stranded array-immobilized strands is the first array strand and the other is the second array strand;
   (i) annealing the non-array first universal primer to the region of the second array strand complementary to the first universal primer;
   (j) extending the non-array first universal primer annealed to the second array strand to form a third intermediate that comprises the second array strand and a complementary non-array strand that comprises the first and second array probes on opposite ends of the target DNA sequence;
   (k) denaturing the third intermediate to yield the non-array strand;
   (l) subjecting the non-array strand to multiple rounds of thermal cycling under suitable PCR reaction conditions to amplify the target DNA sequence; and
   (m) optionally, detecting the amplified target DNA sequence.

2. The method of claim 1 wherein a calibration probe sequence is optionally synthesized between the first universal primer and the first sequence-specific probe or between the second universal primer and the second sequence-specific probe.

* * * * *